United States Patent [19]

Feijen et al.

[11] Patent Number: 5,134,192
[45] Date of Patent: Jul. 28, 1992

[54] PROCESS FOR ACTIVATING A POLYMER SURFACE FOR COVALENT BONDING FOR SUBSEQUENT COATING WITH HEPARIN OR THE LIKE

[75] Inventors: Jan Feijen, Hengelo; Gerardus H. M. Engbers, Oldenzaal, both of Netherlands

[73] Assignee: Cordis Corporation, Miami Lakes, Fla.

[21] Appl. No.: 656,406

[22] Filed: Feb. 14, 1991

[30] Foreign Application Priority Data

Feb. 15, 1990 [NL] Netherlands .................... 9000632

[51] Int. Cl.$^5$ ............................................. C08H 1/00
[52] U.S. Cl. .................... 525/54.1; 523/112; 525/433; 525/452; 525/454; 428/423.1; 530/352; 530/380; 427/2; 427/384
[58] Field of Search ............... 523/112; 525/54.1, 433, 525/452, 454; 428/423.1; 530/380, 352; 427/2, 384

[56] References Cited

U.S. PATENT DOCUMENTS

| | | | |
|---|---|---|---|
| 3,577,211 | 5/1971 | Wilson | 8/115.5 |
| 3,826,678 | 7/1974 | Hoffman et al. | 424/35 |
| 4,360,434 | 11/1982 | Kawaguchi et al. | 521/27 |
| 4,521,564 | 6/1985 | Solomon et al. | 525/54.1 |
| 4,526,714 | 7/1985 | Feijen et al. | 536/21 |
| 4,600,652 | 7/1986 | Solomon et al. | 523/112 |
| 4,634,762 | 1/1987 | Feijen et al. | 530/350 |
| 4,678,671 | 7/1987 | Feijen et al. | 424/443 |
| 4,847,139 | 7/1989 | Wolf et al. | 428/409 |

FOREIGN PATENT DOCUMENTS 6807269 11/1968 Netherlands .

OTHER PUBLICATIONS

Article by Gerardus Henricus Maria Engbers, entitled: Development of Heparinized Materials With an Improved Blood Compatibility, Jun. 28, 1990, pp. 147-190.

*Primary Examiner*—Maurice J. Welsh
*Assistant Examiner*—Rachel Johnson
*Attorney, Agent, or Firm*—Gerstman & Ellis, Ltd.

[57] ABSTRACT

A dicarbonyl halide preferably a straight-chain-alkyl dicarbonyl dihalide, may be used to activate a substrate surface of preferably polyurethane or polyamide. Optionally, an amine-end blocked polymer may be reacted with the resulting activated surface by reaction between amine and dicarbonyl halide groups. Then, a material to be covalently bonded to said surface, such as heparin, may be reacted with free amine groups bonded to the surface by a carbodiimide process or the like.

23 Claims, No Drawings

PROCESS FOR ACTIVATING A POLYMER SURFACE FOR COVALENT BONDING FOR SUBSEQUENT COATING WITH HEPARIN OR THE LIKE

BACKGROUND OF THE INVENTION

This invention relates to a process for activating a substrate surface to render the surface bondable to a material to be immobilized thereon by covalent bonding.

Prepared surfaces are known, as well as methods for their production. These surfaces can serve as a base or substrate for the materials to be immobilized thereon, with the result that the surface acquires contemplated desired properties. Such a prepared surface is applied for example in materials used in medical devices such as catheters and membranes, for in vivo applications in which the material surface is rendered blood compatible by immobilizing thereon a physiological compound, such as heparin, as described in Dutch patent application No. 8701337 and elsewhere.

It is an object of the invention to provide a new process for such activation having improved bonding and a more general function so that the activated surface can serve as a base for immobilizing thereon a considerably broader selection of materials than only physiologically active compounds such as heparin, and to provide such a surface with a prolonged service life.

DESCRIPTION OF THE INVENTION

The invention relates to the steps of selecting a substrate or base from materials containing a group reactive to a carbonyl halide group, followed by activation of the substrate by exposure to the action of a compound containing at least one carbonyl halide group and preferably two such groups.

According to a further embodiment of the process of the invention, for example for better controllability of the reaction velocity of covalently bonding the compound to the substrate surface, the procedure to be followed may comprise: activating the substrate with a solution of the above compound, where the solution comprises a solvent which is substantially not reactive to the substrate material and carbonyl halide groups. A dialkyl ether is suitable, especially those having about 2 to 8 carbon atoms, and many other solvents.

In the process according to the invention the substrate is preferably selected from a material in which the activation reaction leads to bonding of the carbon atom of the carbonyl halide group to a nitrogen atom of the substrate. The substrate is advantageously a polyurethane or a polyamide material. Thus, preferably the substrate is a polymer having nitrogen atoms in the chain, with carbonyl halide groups bonding to such nitrogen atoms between ends of the chain to form N-substituted urethane groups with polyurethane substrates and N-substituted amide groups with polyamide substrates.

The compound to be used in the process according to the invention preferably contains two or more of such carbonyl halide groups. It may be a compound which in addition to the one or more carbonyl halide groups also contains one or more protected or unprotected other functional groups. Preferably, the compound to be used in the process according to the invention has the formula ClOC-R-COCl in which R represents an aliphatic or aromatic hydrocarbon group, such as phenylene or 1,4-butadienyl, or preferably a straight-chain alkylene group containing one or more carbon atoms more preferably a straight-chain alkylene group containing 5 to 20 carbon atoms, in particular a straight-chain alkylene group containing 8 carbon atoms to form sebacoyl dichloride (decanedioyl dichloride), or alkylene groups of more than 8 carbon atoms. Also, the dichloride of malonic acid (propanedioyl dichloride) may be used. A concentration of about 0.1 to 0.5 mole per liter of said compound is typically used.

If, for practical purposes, the duration of the activation reaction is not critical (for example if a duration of about 3 hours is not inconvenient) it is often not necessary to use a catalyst. If, however, reaction times shorter than about 3 hours are wished, as is often the case in industrial applications, then it may be advantageous to use a catalyst, and/or the process may be carried out at higher temperatures and/or at higher diacyldichloride concentrations, or even with pure, non-dissolved diacyldichloride, for faster reaction. An example of a catalyst to be used in the activation reaction is 4-N, N-dimethylaminopyridine (DMAP). In some cases, the use of DMAP may also be disadvantageous owing to the fact that during the activation reaction the use of this compound could be conducive to damage to the substrate surface.

Besides, in the process according to the invention a hydrogen halide acceptor, such as pyridine or triethylamine, may be included in the activation solution, because this is also conducive to the reaction proceeding smoothly.

Within the framework of the preparation of a substrate having a biocompatible surface, especially a blood compatible surface, by immobilizing on the substrate surface a physiologically active compound, the activity of the immobilized physiologically active compound, e.g. heparin, decreases, as is well-known, according as its distance from the substrate surface decreases. Therefore, a spacer compound for increasing the distance from the physiologically active compound to the substrate surface is desirable, e.g. an aliphatic hydrocarbon or a polyether with terminal functional groups such as terminal amino groups, which may be included in the compound chain with which the immobilized, physiologically active compound is connected to the substrate surface. Such a spacer compound is commercially sold by Texaco under the trade name of Jeffamine. In the presence of DMAP the use of Jeffamine in concentrations above a specific value may give rise to undesirable changes in the substrate surface, such as in a substrate of polyurethane. In case of the poly(ester urethane) materials used in the examples given below, for instance, it is advisable to maintain a concentration of 40 mg. of Jeffamine per ml. of solvent as an upper limit.

Another compound to be used as a spacer compound are proteins, such as human albumin.

In the subsequent reaction after the activation of the substrate surface, a polyether spacer compound having terminal amino groups such as Jeffamine, can react with and bond to the substrate surface by means of the carbonyl halide groups of the activated substrate. The remaining amino groups of the spacer compound may then be used for the immobilization by bonding of a physiologically active compound, for example anticoagulants such as heparin.

If desired, a protein conjugate such as an albumin-heparin conjugate can directly be bonded, for example through the amine groups of the albumin moiety, to carbonyl groups of an activated substrate in a single step, and can show good anticoagulant activity without using any other spacer.

The bonding of heparin to remaining amino groups of the spacer compound may take place in a manner analogous to the methods of bonding heparin to albumin to obtain heparin-albumin conjugates as described in U.S. Pat. Nos. 4,634,762; 4,678,671; and 4,526,714. The process comprises the reaction of heparin with albumin in an aqueous medium in the presence of a bonding agent, forming an amide bond. A bonding agent such as EDC (N-ethyl-N'-(3-dimethylaminopropyl)-carbodiimide hydrochloride) can be used. An alternative known manner of bonding heparin to the remaining amino groups is based on a reductive amination reaction between aldehyde-functionalized heparin and Jeffamine using sodium cyanoborohydride as the reductive agent.

Within the scope of the invention, as in the earlier mentioned process known from Dutch patent application No. 8701337, the physiological action of a compound immobilized by this invention may be among others an anticoagulating effect, preferably resulting from heparin or a protein conjugate thereof, the prevention of platelet deposition with albumin, a prostaglandin, or the like, or a fibrinolytic agent such as urokinase and/or streptokinase, or a combined physiological effect resulting from the co-immobilization of for instance two or more of these compounds.

In the process according to the invention an acid halide that can also be employed advantageously is a polyether provided with terminal carbonyl halide groups. In this case the subsequent reaction in which a physiologically active compound is immobilized on the substrate surface may no longer require that a separate spacer compound is included, which results in a simpler process.

In addition to the advantage obtained with the invention, namely improved bonding and a substantial extension of the range of materials that can be immobilized on the activated surface, it is a further advantage that the activation reaction using an acid halide of more than 3 carbon atoms involves little or no risk of the substrate surface being damaged. This is of importance, e.g. when the substrate material is a polyurethane material. The invention also is a simple process in which a substrate surface can be activated in a few steps resulting in a substrate that can serve to immobilize a material suitably selected for its properties thereon in a subsequent reaction. Also in this invention, activation and bonding takes place at intervals along the substrate polymer chain and not just at the polymer ends. Thus better surface coverage with a desired physiologically active compound or the like can be achieved.

The invention will be illustrated by the examples given below.

EXAMPLE 1

Poly(ester urethane) 60 by 20 mm. sheets having a thickness of 0.45 mm were used ("Estane"), with the sheets being prepared by a molding compression technique. The poly(ester urethane) films were cleaned with an ethanol/water mixture under ultrasonic shaking using an ultrasonic shaking bath. The films were then rinsed with an ethanol/water mixture and dried under vacuum at 60° C. for 16 hours.

Then, ten poly(ester urethane) sheets were added to 20 ml. of a solution of DMAP in diethylether (6 mM) to which successively decanedioyl dichloride was added to a concentration of 0.31M. The activation was carried out at room temperature and the activation time was 3 hours. During activation continuous agitation was effected.

Five sheets were then transferred to a flask containing 50 ml. of a solution of an amino end blocked poly(ethylene oxide) with a molecular weight of about 1000 g/mol (Jeffamine ED 900, 100 mg/ml.) and DMAP (6 mM). The other sheets (control sheets) were transferred to a flask containing 50 ml diethylether only. Both flasks were shaken for 3 hrs. at room temperature. The sheets were then washed with diethylether, water, 4M NaCl in water, and again water, and then analyzed with regard to the surface concentration of amine groups and surface morphology. This number was $1.7 \times 10^{-3} \pm 0.3 \times 10^{-3}$ μmol/cm$^2$. For control surfaces a number of amino groups of $0.1 \times 10^{-3}$ μmol/cm$^2$ was determined.

Poly(ester urethane) films which had been treated with a solution of Jeffamine and DMAP (reaction conditions as stated above) in diethylether, without being activated first, had a surface amine group concentration of $0.8 \times 10^{-3} \pm 0.1 \times 10^{-3}$ μmol/cm$^2$, whereas for surfaces treated with a solution of DMAP (reaction conditions as stated above) without Jeffamine nor being activated, an amine group number of $0.1 \times 10^{-3}$ μmol/cm$^2$ was determined.

Under the conditions of the above experiment, when sebacoyl (decanedioyl) dichloride is replaced with any of succinyl, glutaryl, adipoyl, or isophthaloyl dichlorides, the corresponding number of amino groups per surface unit after such treatment does not significantly exceed the number of amino groups per surface unit found on control surfaces.

EXAMPLE 2

The same poly(ester urethane) substrate was activated in a solution of 0.22M decanedioyl dichloride in diethylether, for 3 hours under continuous agitation. After activating and rinsing with diethyl ether the substrate was transferred to an aqueous solution containing 20 mg/ml. of $^{14}$C-labelled albumin. After 3 hours reaction at room temperature the surface was rinsed with successively water, 4M NaCl aqueous solution and again water, followed by determining the amount of immobilized albumin. The determined amount was $5.9 \pm 0.7$ μg/cm$^2$. For a control surface that was not activated, but was incubated in the $^{14}$C-labelled albumin solution, the amount of physically adsorbed albumin was $2.0 \pm 0.1$ μg/cm$^2$.

EXAMPLE 3

The same poly(ester urethane) substrate was activated in pure decanedioyl chloride for 30 minutes at room temperature. After activation, the substrate was dipped into dry diethyl ether to remove unreacted decanedioyl chloride. Then the substrate was transferred to an aqueous solution containing 20 mg/cm$^3$ $^{14}$C-labelled albumin. After 3 hours reaction at room temperature the substrate was rinsed with successively water, 4M NaCl in water, and again water. The amount of immobilized albumin was $2.0 \pm 0.1$ μg/cm$^2$. On control surfaces that had been subjected to the same treatment, with the exception of the sebacoyl chloride being present during activation, the amount of immobilized albumin was 0.6±0.1 μg/cm².

EXAMPLE 4

The poly(ester urethane) substrate was activated in a 0.12M decanedioyl dichloride solution in diethylether for 2 hours under continuous agitation. After activation the substrate was rinsed with diethylether and then immersed in a solution of Jeffamine in diethylether (20 mg/ml) for three hours also under continuous agitation. Then the substrate was rinsed using diethylether, water, 4M NaCl in water and again water. When heparin is covalently coupled to such surface by the well known carbodiimide method, it is possible after 4 hours of reaction between heparin and the PEO modified surface to obtain a surface concentration of heparin on said substrate of 1.4 μg/cm²±0.14. The carbodiimide method may be performed in accordance with any of the following articles: W. E. Hennink et al. "Covalently Bound Conjugates of Albumin and Heparin: Synthesis, Fractionation and Characterization", Thromb. Res. 29, 1–13, 1983; The article by P. W. Heymann, et al. entitled "Heparinized Polyurethanes: In vitro and In vivo Studies", J. Biomed. Mat. Res. 19, 419–436 (1985); and the article by I. Danishessky, et al. "Preparation of Heparin Linked Agarose and its Interaction with Plasma", Thromb Research, 4, 237–246, (1974).

When the same process is performed without EDC, after 4 hours, the surface concentration of heparin on the substrate can be 1.24 μg/cm²±0.14. Surfaces heparinized in the presence of EDC are particularly stable in plasma. After 24 hours of incubation in plasma, only 3 percent of the initial amount of immobilized heparin was lost. For surfaces heparinized without using EDC, 22 percent of the surface-associated heparin was released in 24 hours incubation in plasma.

EXAMPLE 5

Poly(ester urethane) sheets with dimensions of 60×20×0.45 mm. were prepared and cleaned as described in example 1. Ten sheets were quickly rinsed with diethylether and then added to a flask containing 20 ml. of a solution of DMAP (6 mM) in diethylether. Then malonyl (propanedioyl) dichloride was added to a final concentration of 0.31M., followed by shaking of the flask for three hours at room temperature. Five sheets were then transferred to a flask containing 50 ml. of a solution of an amino end blocked poly(ethylene oxide) with a molecular weight of about 1000 gr/mol (Jeffamine, 100 mg/ml., and DMAP to a concentration of 6 mM. The other sheets (control sheets) were transferred to a flask containing 50 ml. diethylether only. Both flasks were shaken for 3 hrs. at room temperature, whereafter the sheets were washed with diethylether, water, 4M NaCl in water, and again water, and then analyzed with regard to the surface concentration of amine groups and surface morphology.

The amount of amine groups on the sheets which were treated with Jeffamine of about 2.6 $10^{-3}$ μmol/cm² was about 8 times higher as the amount of amine groups on the control sheets (0.3 $10^{-3}$ μmol/cm²). This concentration was also higher than the concentration of amino groups of the sheets of Example 1 which were activated with sebacoyl dichloride. Also the concentration of amine groups of control surfaces was higher than the concentration of amine groups of the control surfaces of Example 1. In the analysis of the surface morphology, surface damage was noted in the form of microscopic pits in this experiment using malonyl dichloride, whereas no significant surface damage was observed for the control surface of example 1 which were activated with sebacoyl chloride.

Desired organic materials may be bonded to the substrate produced by any conventional technique of bonding with the bonded amino groups placed on the substrate by the above method. For example, albumin or heparin may be so bonded by means of the carbodiimide process referred to above, or any other known covalent bonding process.

EXAMPLE 6

Poly(ester urethane) discs of 1 cm. radius were punched out of poly(ester urethane) sheet which has been prepared and cleaned as described in example The discs were activated in a solution of decanedioyl dichloride in diethylether (0 22M) under shaking at room temperature for three hours. Then the surfaces were quickly rinsed with diethylether and immersed in a solution of $^{14}C$-radiolabeled albumin-heparin conjugate (10 mg/ml.) in phosphate buffered saline (PBS) for 1 hour. By way of control, discs were immersed in a solution of $^{14}C$-radiolabeled albumin-heparin conjugate (10 mg/ml.) in phosphate buffered saline PBS without being activated first. Then the discs were rinsed with PBS, 4M NaCl in PBS, and finally with water, and then analyzed with regard to the amount of surface bound albumin-heparin conjugate.

For discs which had been activated with a solution of decanedioyl dichloride in diethylether a surface concentration of albumin-heparin conjugate of 0.75±0.14 μg/cm² was determined, whereas, on the control discs onto which the albumin-heparin conjugate was physically absorbed the surface concentration of albumin-heparin conjugate was only 0.17±0.01μg/cm².

Study of the stability of the immobilized albumin-heparin conjugate showed that the albumin-heparin conjugate which had been immobilized after sebacoyl dichloride activation of the surface was stable in plasma, PBS, and a protein solution containing albumin, fibrinogen, and immunoglobulin (at physiological concentrations) for at least 24 hrs. For poly(ester urethane) discs with physically adsorbed albumin-heparin conjugate, the loss of albumin-heparin conjugate after 24 hours incubation in plasma or the protein solution was both about 50%, but the adsorbed albumin-heparin conjugate layer was stable in PBS.

EXAMPLE 7

Poly(ester urethane) discs similar to Example 6 were activated by immersing the discs in pure decanedioyl dichloride for 15 minutes. Then the surfaces were quickly rinsed with diethylether and immersed for 1 hour in a solution of $^{14}C$-radiolabeled albumin-heparin conjugate (10 mg/ml.) in phosphate buffered saline (PBS). After the discs were rinsed with PBS, 4M NaCl in PBS, and finally water, an amount of surface bound albumin-heparin conjugate of 1.42±0.30 μg/cm² was determined, and the surfaces proved to be stable in plasma, PBS, and protein solution containing albumin, fibrinogen and immunoglobulin (see Example 6) for at least 24 hrs.

EXAMPLE 8

Poly(ester urethane) films (see Example 1) were activated in a solution of sebacoyl dichloride (0.22M) in diethylether in the presence of DMAP (6 mM). During the activation time of 3 hours continuous agitation was applied. Then the films were quickly rinsed with diethylether and to each of three flasks, containing a solution of DMAP (6 mM) and Jeffamine in diethylether, a quarter of the activated films was added. The Jeffamine concentrations of the three solutions in the flasks were 20 mg/ml, 40 mg/ml and 100 mg/ml. The remaining quarter of activated films was added to a flask containing a solution of DMAP (6 mM) in diethylether without Jeffamine. After 3 hours reaction under continuous agitation the sheets were rinsed and diethylether, water, 4M NaCl in water, and then again water, and then analyzed with regard to the surface amine group concentration. For surfaces which were reacted in solutions with Jeffamine concentrations of 0, 20, 40 and 100 mg/ml, surface amine group concentrations were determined of respectively $0.12.10^{-3} \pm 0.01.10^{-3}\ \mu mol/cm^2$; $10.9.10^{-3} \pm 1.5.10^3\ \mu mol/cm^2$; $11.9.10^{-3} \pm 1.4.10^{-3}\ \mu mol/cm^2$; and $10.6.10^{-3} \pm 1.6.10^{-3}\ \mu mol/cm^2$.

The above has been offered for illustrative purposes only, and is not intended to limit the scope of the invention, which is as defined in the claims below.

That which is claimed is:

1. In a process for activating the surface of a substrate to render it covalently bondable with a material to be immobilized thereon, which comprises, providing a substrate which comprises an organic polymer material having a plurality of nitrogen containing reactive groups between the ends of the molecules of said polymer, which reactive groups are reactive with carbonyl halide groups, and exposing the surface of said substrate to a compound containing at least two carbonyl halide groups per molecule, whereby said compound is bonded to the surface of said substrate to form an activated surface by linkage to nitrogen atoms of said reactive groups by reaction between said nitrogen containing reactive groups and said carbonyl halide groups, said compound being exposed to the substrate surface in sufficient concentration to result in an activated substrate surface having sufficient pendant carbonyl halide groups to permit the subsequent bonding of a nitrogen-containing compound to said surface.

2. The process of claim 1 in which said compound containing at least two carbonyl halide groups is applied to said substrate surface while dissolved in a solvent in a concentration of 0.1 to 0.5 mole per liter, said solvent being substantially nonreactive to said substrate surface and to said carbonyl halide groups.

3. The process of claim 1 in which said substrate material is a polyurethane.

4. The process according to claim 1 in which said substrate material is a polyamide.

5. The process of claim 1 in which said compound is decanedioyl dichloride.

6. The process of claim 1 in which said compound is a polyethylene oxide having terminal carbonyl halide groups.

7. The process of claim 1 in which said compound is a carbonyl chloride of the formula ClOC-R-COCl in which R represents an alkylene group of 5 to 20 carbon atoms.

8. The process of claim 1 in which said compound is propanedioyl dichloride.

9. The process of claim 1 in which said activated surface of the substrate is subsequently reacted with an amine-terminated polymer, whereby said activated surface comprises free amino active groups.

10. The process of claim 9 in which heparin is thereafter bonded to active amino groups of said surface.

11. The process of claim 9 in which said amine-terminated polymer comprises an amine-terminated polymer of polyethylene oxide.

12. The process of claim 1 in which said activation reaction takes place in the presence of at least one of a catalyst and a hydrogen halide acceptor.

13. The process of claim 1 in which said activated surface of the substrate is subsequently bonded to an albumin-heparin conjugate.

14. A process for activation of a substrate surface which comprises a polyurethane or polyamide material to render said surface bondable to a material by covalent bonding, which method comprises: exposing decanedioyl dichloride to said surface while dispersed in a solvent which is essentially nonreactive to the substrate material and said decanedioyl dichloride, to promote bonding between said decanedioyl dichloride and nitrogen atoms of said substrate; followed by reacting said bonded substrate surface with an amine-terminated polyethylene oxide to form amide linkages between the bonded decanedioyl dichloride groups and the polyethylene oxide, to provide reactive amino groups to said substrate surface, and thereafter causing the covalent bonding of heparin to said reactive amino groups to covalently bond said heparin to said substrate surface.

15. The process of claim 14 in which said dispersion of said decanedioyl chloride is in a dialkyl ether, with the decanedioyl chloride being present in a concentration of 0.1 to 0.5 mole per liter.

16. The method of claim 15 in which said heparin is bonded to said substrate by means of a carbodiimide amide bond forming agent.

17. The method of claim 16 in which said substrate is in the form of a catheter.

18. A process for activation of a substrate surface which comprises a polyurethane or polyamide material to render said surface bondable to a material by covalent bonding, which method comprises: exposing an alkylenedioyl dichloride of 7 to 22 carbon atoms to said surface while suspended in a solvent which is essentially non-reactive to the substrate material and said alkylenedioyl dichloride, to promote bonding between said alkylenedioyl dichloride and nitrogen atoms of said substrate; followed by reacting said bonded substrate surface with a protein-heparin conjugate to covalently bond said heparin to said substrate surface.

19. The process of claim 18 in which said solvent is in a dialkyl ether, and the alkylenedioyl dichloride is decanedioyl dichloride.

20. The process of claim 19 in which said decanedioyl dichloride is present in a concentration of 0.1 to 0.5 mole per liter.

21. The process of claim 19 in which said protein-heparin conjugate is an albumin-heparin conjugate.

22. The process of claim 18 in which said alkylenedioyl dichloride is decanedioyl dichloride.

23. The process of claim 22 in which said decanedioyl dichloride is present in a concentration of 0.1 to 0.5 mole per liter.

* * * * *